United States Patent
Kim

(10) Patent No.: US 12,183,462 B2
(45) Date of Patent: Dec. 31, 2024

(54) METHOD FOR PREDICTING LUNG CANCER DEVELOPMENT BASED ON ARTIFICIAL INTELLIGENCE MODEL, AND ANALYSIS DEVICE THEREFOR

(71) Applicant: BIOLINK Inc, Daegu (KR)

(72) Inventor: Hae Won Kim, Daegu (KR)

(73) Assignee: BIOLINK Inc., Daegu (KR)

( * ) Notice: Subject to any disclaimer, the term of this patent is extended or adjusted under 35 U.S.C. 154(b) by 440 days.

(21) Appl. No.: 17/641,692

(22) PCT Filed: Apr. 3, 2020

(86) PCT No.: PCT/KR2020/004554
§ 371 (c)(1),
(2) Date: Mar. 9, 2022

(87) PCT Pub. No.: WO2021/049729
PCT Pub. Date: Mar. 18, 2021

(65) Prior Publication Data
US 2022/0301714 A1    Sep. 22, 2022

(30) Foreign Application Priority Data
Sep. 10, 2019 (KR) .......................... 10-2019-0112244

(51) Int. Cl.
*G06V 10/82* (2022.01)
*A61B 6/03* (2006.01)
*G06T 7/00* (2017.01)
(Continued)

(52) U.S. Cl.
CPC .............. *G16H 50/20* (2018.01); *A61B 6/032* (2013.01); *A61B 6/037* (2013.01); *G06T 7/0014* (2013.01);
(Continued)

(58) Field of Classification Search
CPC ........ G16H 50/20; G16H 30/40; G16H 50/70; G16H 40/67; G16H 50/30; A61B 6/032;
(Continued)

(56) References Cited

U.S. PATENT DOCUMENTS

2007/0237373 A1    10/2007   Kiraly et al.
2018/0116620 A1     5/2018   Chen et al.
(Continued)

FOREIGN PATENT DOCUMENTS

JP          2016-012345 A       1/2016
KR    10-2017-0016778 A         2/2017
(Continued)

OTHER PUBLICATIONS

International Search Report for PCT/KR2020/004554 mailed Jul. 28, 2020 from Korean Intellectual Property Office.
(Continued)

*Primary Examiner* — Dov Popovici
(74) *Attorney, Agent, or Firm* — PNKIP LLC

(57) ABSTRACT

A method for determining a probability of developing lung cancer by using an artificial intelligence model, includes: receiving, by an analysis device, a chest fluorodeoxyglucose (FDG) PET/CT image for a sample; inputting, by the analysis device, the F-18 FDG PET/CT image to a first classification neural network, and outputting prediction information related to development of lung cancer for the sample; and predicting, by the analysis device, a probability of developing lung cancer for the sample on the basis of the prediction information. The first classification neural network is trained by using chest F-18 FDG PET/CT images for healthy people and training images excluding lung cancer regions from chest F-18 FDG PET/CT images for lung cancer patients.

19 Claims, 9 Drawing Sheets

(51) Int. Cl.
  *G06V 10/22* (2022.01)
  *G06V 10/764* (2022.01)
  *G06V 10/774* (2022.01)
  *G16B 20/00* (2019.01)
  *G16H 30/40* (2018.01)
  *G16H 50/20* (2018.01)
  *G16H 50/70* (2018.01)

(52) U.S. Cl.
  CPC ............ *G06V 10/22* (2022.01); *G06V 10/764* (2022.01); *G06V 10/774* (2022.01); *G06V 10/82* (2022.01); *G16B 20/00* (2019.02); *G16H 30/40* (2018.01); *G16H 50/70* (2018.01); *G06T 2207/10081* (2013.01); *G06T 2207/10104* (2013.01); *G06T 2207/20076* (2013.01); *G06T 2207/20081* (2013.01); *G06T 2207/20084* (2013.01); *G06T 2207/30061* (2013.01); *G06V 2201/03* (2022.01)

(58) Field of Classification Search
  CPC ..... A61B 6/037; A61B 6/5217; G06T 7/0014; G06T 2207/10081; G06T 2207/10104; G06T 2207/20076; G06T 2207/20081; G06T 2207/20084; G06T 2207/30061; G06T 2207/20132; G06T 7/0012; G06V 10/22; G06V 10/764; G06V 10/774; G06V 10/82; G06V 2201/03; G16B 20/00; G16B 20/20; G16B 40/20; G06N 3/02

USPC ....... 382/131, 128, 130, 132, 133, 155, 156, 382/157, 158, 159, 160, 161
  See application file for complete search history.

(56) References Cited

U.S. PATENT DOCUMENTS

| | | | |
|---|---|---|---|
| 2021/0225511 A1* | 7/2021 | Kiraly | G06F 18/213 |
| 2022/0180514 A1* | 6/2022 | Vlasimsky | G06T 3/40 |
| 2024/0124941 A1* | 4/2024 | Poore | G16H 50/70 |

FOREIGN PATENT DOCUMENTS

| | | |
|---|---|---|
| KR | 10-2019-0049524 A | 5/2019 |
| KR | 10-2019-0092299 A | 8/2019 |

OTHER PUBLICATIONS

Korean Office Action for related KR Application No. 10-2019-0112244 mailed Jan. 28, 2021 from Korean Intellectual Property Office.

Moritz Schwyzer et al., "Automated detection of lung cancer at ultralow dose PET/CT by deep neural networks—Initial results", Lung Cancer, Nov. 3, 2018, pp. 170-173, vol. 126.

* cited by examiner (A)

(B)

METHOD FOR PREDICTING LUNG CANCER DEVELOPMENT BASED ON ARTIFICIAL INTELLIGENCE MODEL, AND ANALYSIS DEVICE THEREFOR

CROSS-REFERENCE TO PRIOR APPLICATIONS

This application is a National Stage Patent Application of PCT International Patent Application No. PCT/KR2020/004554 (filed on Apr. 3, 2020) under 35 U.S.C. § 371, which claims priority to Korean Patent Application No. 10-2019-0112244 (filed on Sep. 10, 2019), which are all hereby incorporated by reference in their entirety.

BACKGROUND

The following description relates to a technique for determining a probability of developing lung cancer by using a medical image.

Lung cancer has few symptoms in the early stages of development, and therefore is usually detected in the later stage. The 5-year relative survival rate of inoperable advanced lung cancer, which accounts for 50 to 70% of all lung cancer cases, is about 6.1% (based on 2011-2015). More than 9 out of 10 (94%) advanced lung cancer patients die within 5 years.

For early detection of lung cancer, the medical community recommends performing a low-dose CT every year. A low-dose computed tomography (CT) is highly likely to detect lung cancer earlier than chest X-rays.

SUMMARY

A lung cancer diagnosis rate with a low-dose computed tomography (CT) is very low at 0.3 to 2.3%. The low-dose CT shows false-positive results about 20% of the time. A false-positive diagnosis causes the problem of unnecessary invasive diagnostic tests. In addition, there is a risk of causing cancer due to radiation exposure when the low-dose CT is repeatedly performed.

A technology to be described below provides a technique for automatically determining a probability of developing lung cancer based on a diagnostic image using an artificial intelligence (AI) model. In addition, a technology to be described below provides a technique for determining a probability of developing lung cancer based on a diagnostic image and omics data using an artificial intelligence (AI) model.

A method for determining a probability of developing lung cancer by using an artificial intelligence model includes receiving, by an analysis device, a chest F-18 fluorodeoxyglucose (FDG) positron emission tomography (PET)/CT image for a sample, inputting, by the analysis device, the F-18 FDG PET/CT image to a first classification neural network and outputting prediction information related to development of lung cancer for the sample, and predicting, by the analysis device, a probability of developing lung cancer for the sample based on the prediction information.

The analysis device may receive omics data for the sample, input the omics data to a second classification neural network, and output second prediction information on the probability of developing lung cancer for the sample.

An analysis device includes an input device configured to receive a chest F-18 FDG PET/CT image for a sample, a storage device configured to store a first classification neural network that generates prediction information on the probability of developing lung cancer using the chest F-18 FDG PET/CT image, and a computing device configured to input the received F-18 FDG PET/CT image to the first classification neural network to predict a probability of a subject developing lung cancer.

The first classification neural network may be trained using a chest F-18 FDG PET/CT image for a healthy person and a training image excluding a lung cancer region from a chest F-18 FDG PET/CT image for a lung cancer patient.

A method for determining a probability of developing lung cancer by using an artificial intelligence model includes inputting, by an analysis device, a chest F-18 FDG PET image for a sample to a first classification neural network, outputting first prediction information related to development of lung cancer for the sample, inputting, by the analysis device, a chest CT image for the sample to a second classification neural network, outputting second prediction information related to the development of lung cancer for the sample, and predicting, by the analysis device, a probability of developing lung cancer for the sample based on the first prediction information and the second prediction information. The first classification neural network may be trained using a chest F-18 FDG PET image for a healthy person and a first training image excluding a lung cancer region from a chest F-18 FDG PET image for a lung cancer patient, and the second classification neural network may be trained using a chest CT image for a healthy person and a second training image excluding the lung cancer region from the chest CT image for the lung cancer patient.

A technology to be described below predicts a probability of developing lung cancer non-invasively using an artificial intelligence (AI) model. Therefore, the technology to be described below may select patients with a high probability of developing lung cancer which is difficult to determine by the conventional image diagnosis method, thereby enabling intensive management of these patients and increasing the early diagnosis rate of lung cancer. Accordingly, the technology to be described below improves a survival rate of lung cancer patients.

DETAILED DESCRIPTION

Figure 1:
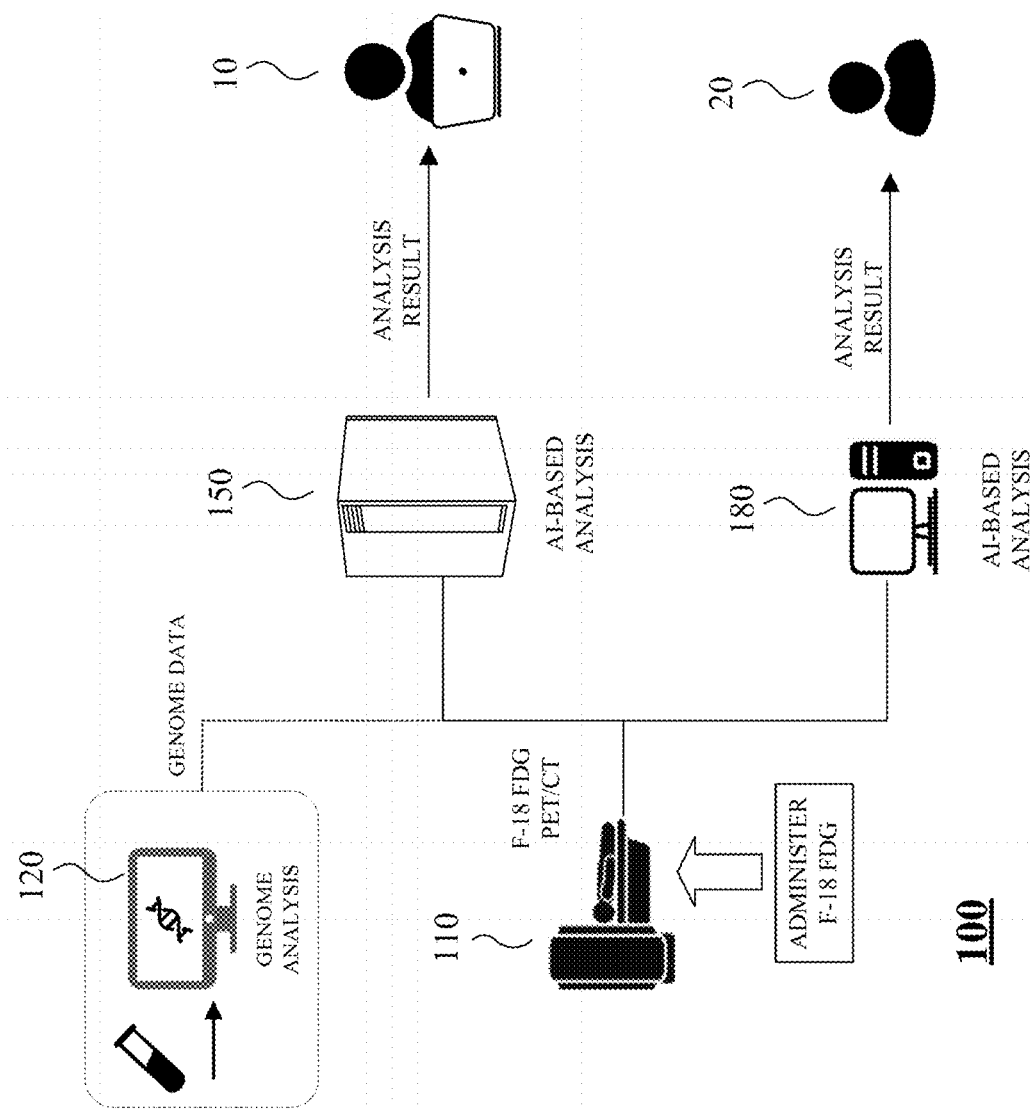
FIG. 1 is an example of a system for predicting development of lung cancer using a medical image.

A technology to be described below may be variously modified and have several embodiments. Therefore, specific exemplary embodiments of the technology to be described below will be illustrated in the accompanying drawings and described in detail. However, this is not intended to limit the technology to be described below to specific embodiments, and the technology can be understood to include all conversions, equivalents, or substitutes included in the technical spirit and technical scope of the technology to be described below.

Terms such as "first," "second," "A," "B," and the like may be used to describe various components, but the components are not to be interpreted to be limited by the terms, which are used only for distinguishing one component from other components. For example, a first component may be named a second component and a second component may also be similarly named a first component, without departing from the scope of the technology to be described below. The term "and/or" includes a combination of a plurality of related described items or any one of the plurality of related described items.

It should be understood that singular expressions do not exclude plural referents unless the context clearly indicates otherwise, and it will be further understood that the terms "comprise" and "have" used in this specification specify the presence of stated features, steps, operations, components, parts, or combinations thereof, but do not preclude the presence or addition of one or more other features, numerals, steps, operations, components, parts, or combinations thereof.

Prior to the detailed description of the drawings, it should be clarified that the components in this specification are only distinguished by their main functions. That is, two or more components to be described below may be combined into one component, or one component may be divided into two or more for each subdivided function. In addition, each of the constituent parts to be described below may additionally perform some or all of the functions of other constituent parts in addition to the main functions of the constituent parts, and some of the main functions of the constituent parts may be performed exclusively by other components.

In addition, in performing the method or the operation method, each of the processes constituting the method may occur differently from the specified order unless a specific order is explicitly described in context. That is, the respective steps may be performed in the same sequence as the described sequence, performed at substantially the same time, or performed in an opposite sequence to the described sequence.

Information and terms used in the following description will be described first.

A user or a subject is a person to be tested. A sample is a sample taken from the user. Thus, a specific sample is also a specific user.

A medical image is an image including medical information on a user (patient). The medical image includes any of various images photographed by various techniques. For example, the medical image is an X-ray image, a computed tomography (CT) image, a magnetic resonance imaging (MRI) image, a positron emission tomography (PET) image, a PET/CT image, or the like. For convenience of explanation below, individual images are expressed as CT, PET, PET/CT, or the like.

CT is a tomography technique using X-rays. PET is a PET technique. In PET, a substance that emits positrons is injected intravenously into a specific part of the body, and then the subject is imaged. With PET, various molecular images such as glucose metabolism, amino acid metabolism, deoxyribonucleic acid (DNA) synthesis, receptor images (somatostatin, etc.), tumor-specific antibodies, and gene images can be acquired depending on a type of radioactive isotope compound injected into the human body.

PET/CT is an imaging technique that combines PET and CT. PET/CT includes both morphological imaging (i.e., CT) and functional imaging (i.e., PET) of a disease. Therefore, PET/CT may be used to diagnose lesions more accurately than a conventional PET scan.

F-18 fludeoxyglucose (FDG) PET/CT is PET/CT using F-18 FDG. F-18 FDG moves into cells like glucose, and an uptake rate varies depending on metabolic activity of the cells. The uptake of F-18 FDG is significantly increased in activated inflammatory cells where glycolysis is actively taking place. Therefore, F-18 FDG PET/CT is useful for monitoring regions where inflammation develops. Researchers (medical staff) may administer a certain amount of F-18 FDG to a subject, and perform F-18 FDG PET/CT using a PET scanner after a certain amount of time has elapsed. Hereinafter, an F-18 FDG PET/CT image is referred to as an F-18 FDG PET/CT or FDG PET/CT.

Omics data is various types of molecular level data that may be obtained by analyzing a sample. For example, the omics data may be at least one of data about a genome, a tranome, a proteome, a metabolome, an epigenome, a lipodome, etc.

Meanwhile, multi-omics analysis is overall integrated analysis of various omics data. With the development of super-speed jetting biological analysis technology, research on the relationships between specific diseases and genotypes through multi-omics analysis is being actively conducted.

The technology to be described below is a technique for determining a probability of developing lung cancer. The technology to be described below predicts the probability of developing lung cancer by analyzing medical images. The technology to be described below may use various medical images showing inflammatory features of a lung region. Hereinafter, it is assumed that the probability of developing lung cancer is predicted using F-18 FDG PET/CT images.

According to the technology to be described below, medical images are analyzed using a machine learning model. As is widely known, there are various types of machine learning models. For the technology to be described below, it is assumed that images are analyzed using an artificial neural network. A deep learning network may be used as the artificial neural network. The deep learning network may be a model such as a deep neural network (DNN), a convolutional neural network (CNN), a recurrent neural network (RNN), or a restricted Boltzmann machine (RBM). A detailed description of the well-known deep learning model will be omitted.

Hereinafter, a device that analyzes an image using an artificial neural network is called an analysis device. The analysis device analyzes the image using a pre-trained artificial neural network. The analysis device may derive an analysis result by inputting a medical image to the artificial neural network. The analysis device may perform certain data processing or signal processing. The analysis device may also analyze omics data together with an image. For example, the analysis device may be implemented as a device such as a personal computer (PC), a smart device, or a server.

Lung cancer is medically known to be caused by various risk factors (smoking, genetics, viruses, environmental factors, etc.). It is recognized that lung cancer risk factors cause chronic inflammatory response in lung parenchyma and progress to lung cancer through genetic modification. That is, it is recognized that inflammation has an etiologic role for lung cancer. Previous studies have mainly focused on the development of image analysis technology or biological markers (C-reactive protein, interleukin, etc.) for determining whether lung nodules are lung cancer or simple benign nodules in patients with lung nodules.

The technology to be described below predicts a probability of developing lung cancer using a user's chest F-18 FDG PET/CT image. Basically, the technology to be described below predicts the probability of users who are not lung cancer patients (healthy people) developing lung cancer. Even healthy people may have certain inflammatory lesions in chest F-18 FDG PET/CT images. Furthermore, healthy people may also have inflammation-related features in chest F-18 FDG PET/CT images that are not clear from the viewer's perspective. Furthermore, the technology to be described below may predict lung cancer by analyzing images of healthy people without lung nodules. The technology to be described below predicts the probability of developing lung cancer using inflammatory features associated with lung cancer.

Inflammation is an important factor in cancer development, and many types of cancer are caused by infection, chronic irritation, and inflammation. Smoking, air pollution, genetic predisposition, exposure to carcinogens (asbestos, radon, etc.), repeated inflammation (tuberculosis, emphysema, pulmonary fibrosis), silicosis, and the like are known as lung-cancer-related factors. These risk factors cause the chronic inflammatory response in the lung parenchyma and cause lung cancer through genetic modification. By comparing and analyzing omics data such as a genome, a tranome, and a protein body related to lung inflammation in lung cancer patients and healthy people, biomarkers suggesting the probability of developing lung cancer may be selected. Therefore, omics data may be additionally used in addition to a medical image in a neural network model for predicting development of lung cancer. It is assumed that markers associated with the development of lung cancer have been previously selected. The marker related to the development of lung cancer may be selected using the results of previous studies. Inflammation-related biomarkers such as C-reactive protein (CRP), an erythrocyte sedimentation rate (ESR), and plasma viscosity (PV) may be selected as markers related to the development of lung cancer.

FIG. 1 is an example of a system 100 for predicting development of lung cancer using a medical image. The system 100 for predicting development of lung cancer includes a medical image scanning device 110 and analysis devices 150 and 180.

The medical image scanning device 110 is an imaging device installed in a medical institution. The medical image scanning device 110 generates images such as CT, PET, and PET/CT for a user. FIG. 1 illustrates one medical image scanning device 110. The system 100 for predicting development of lung cancer may use a plurality of medical images. Accordingly, unlike FIG. 1, different types (plural) of medical image scanning devices may be used. For convenience of description, it is assumed that the medical image scanning device 110 generates an F-18 FDG PET/CT image.

An omics data generation device 120 generates at least one type of omics data by analyzing the sample. The omics data generation device 120 may be a device belonging to the same institution as the medical image scanning device 110, or a device operated by a separate provider. FIG. 1 illustrates an example in which the omics data generation device 120 is a device generating genome data by performing next generation sequencing (NGS) analysis on a sample.

FIG. 1 illustrates an analysis server 150 and an analysis PC 180 as an example of the analysis device. The analysis device can be implemented in various forms. For example, the analysis device may be implemented as a portable mobile device.

The system 100 for predicting development of lung cancer may include either the analysis server 150 or the analysis PC 180. In addition, the system 100 for predicting development of lung cancer may include both of the analysis server 150 and the analysis PC 180.

The analysis server 150 receives the F-18 FDG PET/CT image from the medical image scanning device 110. The analysis server 150 may receive a medical image through a wired or wireless network. The analysis server 150 analyzes the medical image and transmits the analysis result to a user 10. Furthermore, the analysis server 150 may further receive omics data for the sample, and analyze the sample using the omics data together with the medical image.

The user 10 may check the analysis result or image of the analysis server 150 through a user terminal. The user terminal is a device such as a PC, a smart device, or a display device.

The analysis PC 180 receives the F-18 FDG PET/CT image generated by the medical image scanning device 110. The analysis PC 180 may receive the F-18 FDG PET/CT image through the wired or wireless network. Alternatively, the analysis PC 180 may receive the F-18 FDG PET/CT image from media (a universal serial bus (USB), a secure digital (SD) card, a compact disc (CD), etc.) for storing the F-18 FDG PET/CT image. Furthermore, the analysis PC 180 may further receive the omics data for the sample, and analyze the sample using the omics data together with the medical image. The analysis PC 180 analyzes the medical image and transmits the analysis result to a user 20. The user 20 may check the analysis result through the analysis PC 180.

The analysis server 150 or the analysis PC 180 may analyze a medical image using a deep learning model. The analysis server 150 or the analysis PC 180 may analyze the omics data using the deep learning model. The analysis server 150 or the analysis PC 180 may analyze "a medical image" or "a medical image and omics data" to generate information on the probability of the user developing lung cancer.

Figure 2:
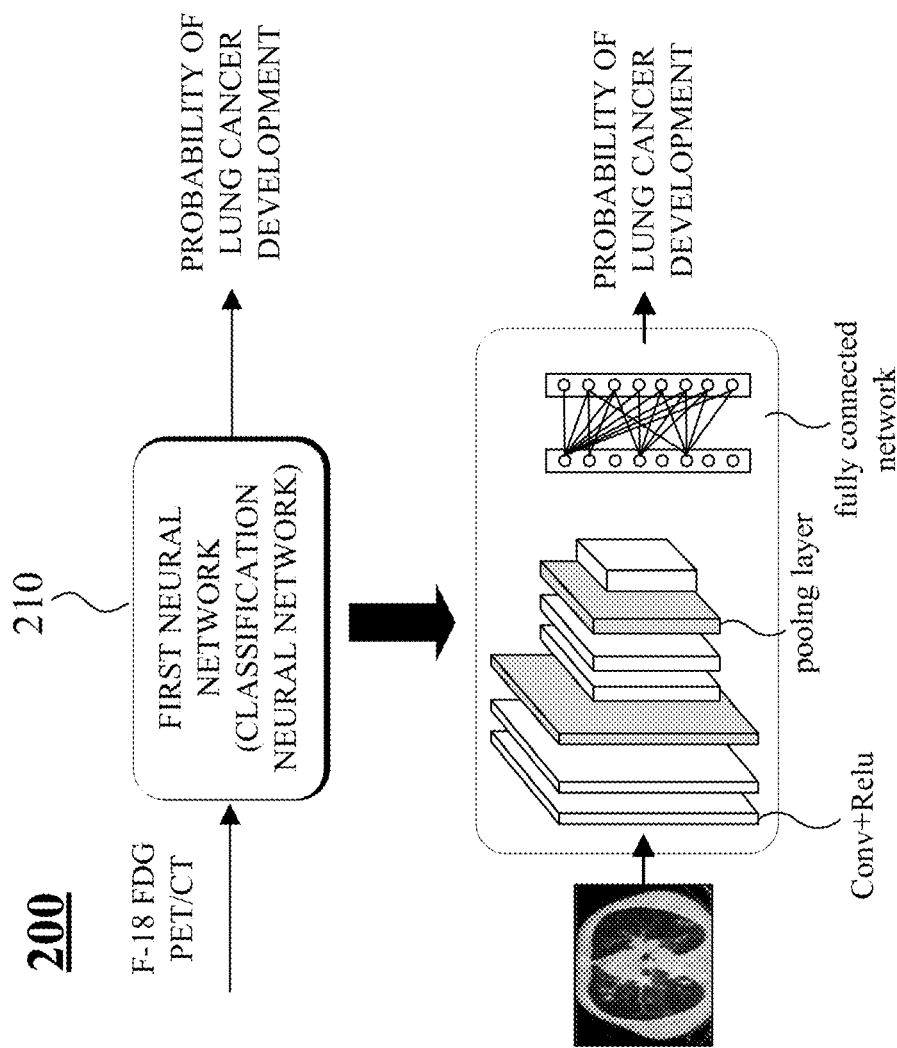
FIG. 2 is an example of a neural network model for predicting development of lung cancer.

FIG. 2 is an example of a neural network model 200 for predicting development of lung cancer. FIG. 2 is the example of the neural network model 200 that can be used in the analysis device for determining a probability of developing lung cancer. FIG. 2 is an example of a neural network model for predicting development of lung cancer using only a medical image.

FIG. 2 is an example of using one neural network (first neural network 210). The first neural network 210 receives the F-18 FDG PET/CT image and outputs the information for determining the probability of developing lung cancer for the corresponding image. Hereinafter, a neural network that determines a probability of developing lung cancer using a medical image is called a classification neural network. The classification neural network may classify a probability of developing lung cancer for a sample (user).

The first neural network 210 may output information such as a high risk or a low risk as a probability of developing lung cancer.

Furthermore, the first neural network 210 may perform multi-classification. For example, the first neural network 210 may predict timing of the probability of developing lung cancer. In this case, the first neural network 210 may also provide information on timing, such as a probability of development within 5 years and a probability of development within 3 years for a sample. Of course, for such an output, the training data needs to provide information on a time from imaging to development.

In FIG. 2, the first neural network 210 may receive only a lung region instead of the entire input image. In this case, it may be necessary to perform pre-processing on the input image. For example, the computer device may pre-process the input image using a seed-based region growing technique.

The first neural network 210 may be a model such as a CNN. The first neural network 210 receives a medical image and outputs information on a probability of developing lung cancer, which is a result of analyzing the medical image. The first neural network 210 needs to be pre-trained. The first neural network 210 may be trained using information on whether or not lung cancer develops from a specific type of training images (either F-18 FDG PET or F-18 FDG PET/CT) and a source (human) of training images. The neural network training process will be described below.

As described above, various models may be used for the neural network model. Typically, a CNN may be used. The CNN may be composed of various types of hierarchical structures. In general a CNN is a network in which a convolutional layer and a pooling layer are composed of several layers. For example, the CNN may have a structure of two max pooling layers of 5 convolutional layers+Relu layers and two fully connected layers.

The convolutional layer outputs a feature map through a convolutional operation on the input image. In this case, a filter that performs the convolutional operation is also called a kernel. A size of the filter is called a filter size or a kernel size. Operation parameters constituting a kernel are called a kernel parameter, a filter parameter, or a weight.

The convolution operation is performed in a window of a constant size. The window may be moved by one space from an upper left to a lower right of the image, and a movement size of each movement may be adjusted. The movement size is called a stride. The convolutional layer performs a convolution operation on all regions of the input image while moving the window in the input image. The convolutional layer may maintain dimensions of the input image after the convolution operation by padding edges of the image.

A nonlinear operation layer is a layer that determines output values from neurons (nodes). The nonlinear computation layer uses a transfer function. The transfer function includes a Relu function, a sigmoid function, and the likes. FIG. 1 illustrates an example of using the convolutional layer and Relu.

The pooling layer sub-samples a feature map obtained as an operation result in the convolutional layer. The pooling operation includes max pooling, average pooling, and the like. In max pooling, the largest sample value in the window is selected. In average pooling, sampling is performed with an average value of values included in the window.

The fully connected layer finally classifies the input image. In FIG. 2, the fully connected layer outputs information on a probability of developing lung cancer.

Figure 3:
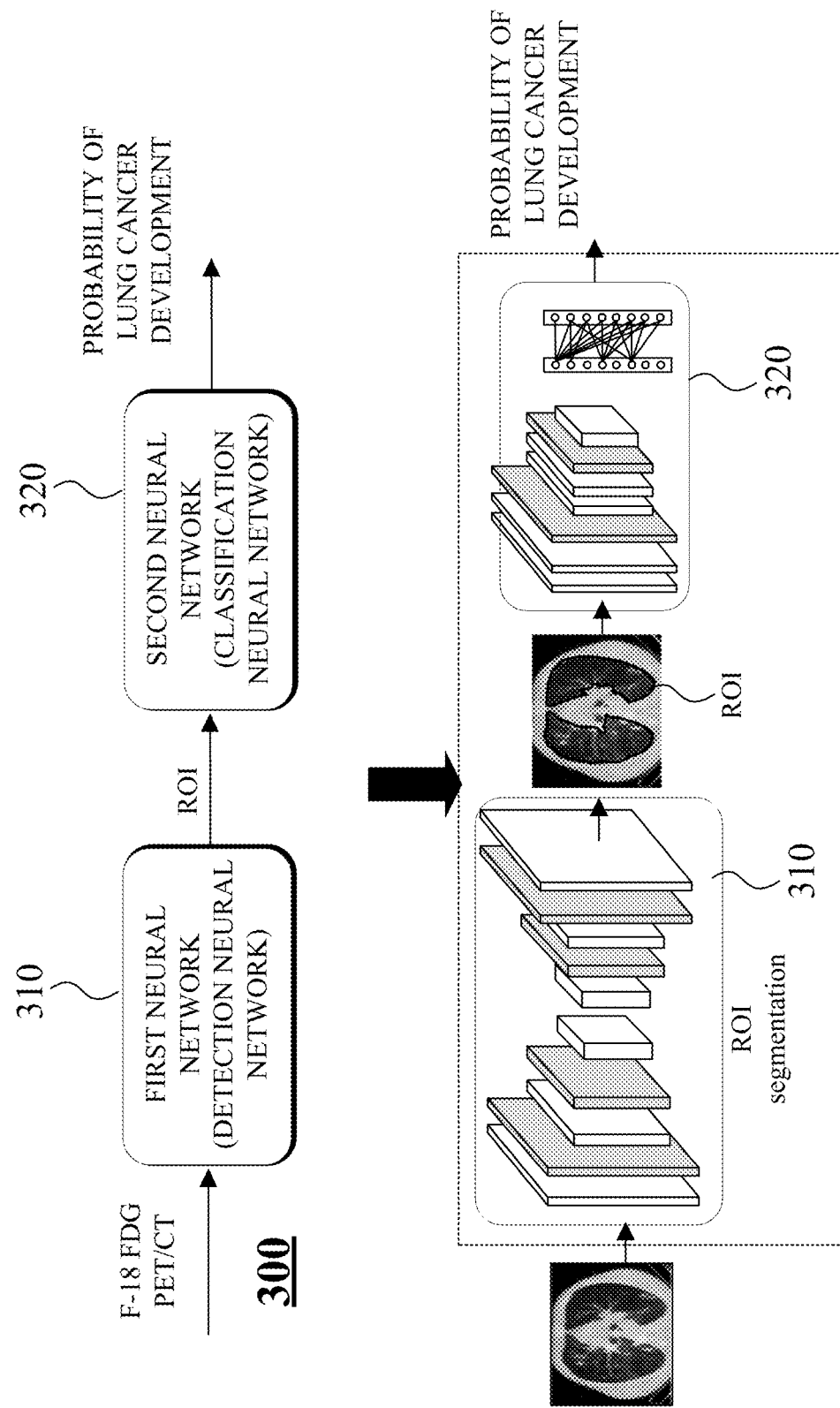
FIG. 3 is another example of the neural network model for predicting development of lung cancer.

FIG. 3 is another example of a neural network model 300 for predicting development of lung cancer. FIG. 3 is an example of using two neural networks (a first neural network and a second neural network). The first neural network 310 and the second neural network 320 may be different types of deep learning models. FIG. 3 is an example of a neural network model for predicting development of lung cancer using only a medical image.

The first neural network 310 detects a region of interest (ROI) in which a desired object exists in a medical image. The first neural network 310 corresponds to a model for detecting (segmenting) a specific region or an object in a medical image. As such, a type of neural network that detects an object in a medical image is called a detection neural network.

The detection neural network identifies an object in a medical image and segments (divides) the object. The detection neural network may be implemented with various types of models. For example, the detection neural network may be a model such as a type of CNN. The detection neural network may have a structure such as an encoder-decoder structure, a fully convolutional network (FCN), and or like.

The first neural network 310 is for object detection, and detects and divides a specific region based on feature information of a medical image. The first neural network 310 may divide a lung region into an ROI in the F-18 FDG PET/CT image. The first neural network 310 needs to be pre-trained to detect the ROI.

The second neural network 320 outputs information on a probability of developing lung cancer by using the input medical image. The second neural network 320 corresponds to the classification neural network. In this case, the second neural network 320 may use an image output from the first neural network 310 as an input image. That is, the second neural network 320 may output the information on the probability of developing lung cancer based on the lung region.

The second neural network 320 may be a model such as a CNN. The second neural network 320 may receive an ROI detected by the first neural network 310 as an input. Alternatively, the second neural network 320 may receive the entire medical image and analyze the image using only the feature information of the ROI. The second neural network 320 outputs information on a probability of developing lung cancer based on the feature information of the ROI. The second neural network 320 needs to be pre-trained. The second neural network 320 may be trained using a training image of the ROI and information on a probability of developing lung cancer matching the image.

The second neural network 320 may output information such as a high risk or a low risk as the probability of developing lung cancer.

Furthermore, the second neural network 320 may perform multi-classification. For example, the second neural network 320 may predict timing of the probability of developing lung cancer. In this case, the second neural network 320 may also provide information on timing, such as a probability of development within 5 years and a probability of development within 3 years for a sample. Of course, for such an output, the training data needs to provide information on a time from imaging to development.

An example of the input medical image and an example of the output information on the probability of developing lung cancer are illustrated in a lower portion of FIG. 3. As an example of the medical image, an F-18 FDG PET/CT image is illustrated. The first neural network 310 detects a lung region that is an ROI in the F-18 FDG PET/CT image. The second neural network 320 receives the image or information output from the model of the first neural network 310 and outputs information on the probability of developing lung cancer. The information on the probability of developing lung cancer may be high-risk or low-risk.

Meanwhile, the information on the probability of developing lung cancer may be information such as a probability of development within 5 years and a probability of development within 3 years.

Figure 4:
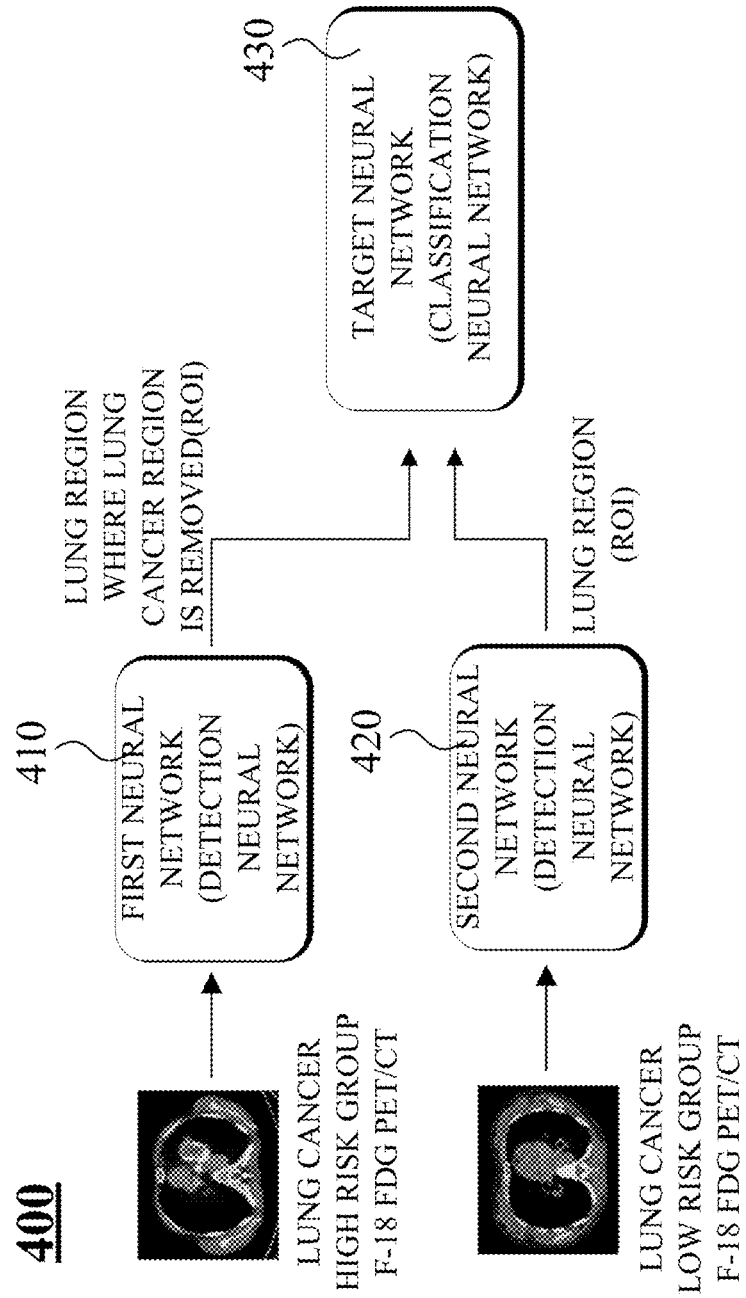
FIG. 4 is an example of a process of training a neural network.

FIG. 4 is an example of a process 400 of training a neural network. FIG. 4 is an example of a process of training a classification neural network. The classification neural network may be trained using F-18 FDG PET/CT images of lung cancer patients and F-18 FDG PET/CT images of healthy people. Although FIG. 4 is described based on the F-18 FDG PET/CT image, when the F-18 FDG PET and CT are used separately, the same process may be performed on each of the F-18 FDG PET and CT.

The training image may be subjected to pre-processing. For example, when the F-18 FDG PET/CT image is used, a PET dicom image and a CT dicom image of 512*512 pixels may be cropped to a size of 256*256 pixels. A determination result of the cropped image may be defined as a two-dimensional one-hot vector. For example, the chest F-18 FDG PET/CT images of healthy people may be classified as a low-risk group and defined as [0,1], and the chest F-18 FDG PET/CT images of lung cancer patients may be classified as a high-risk group and defined as [1,0]. A process of transforming pixel information or text into a single meaningful vector and defining the pixel information is called one-hot encoding.

The first neural network 410 is a neural network for detecting an ROI in images of lung cancer patients. The first neural network 410 detects a lung region in the F-18 FDG PET/CT of the lung cancer high risk group (lung cancer patients). Furthermore, the first neural network 410 detects regions other than lung cancer regions (regions where lung cancer has developed) in the lung region. The first neural network 410 needs to be pre-trained to detect the lung region from which the lung cancer regions have been removed. The first neural network 410 detects regions excluding the lung cancer regions from the images of the lung cancer patients. The regions excluding the lung cancer regions visually correspond to healthy people regions (regions without lung nodules).

A target neural network 430 is the above-described classification neural network. The target neural network 430 outputs information on a probability of developing lung cancer based on the input image. When the target neural network 430 receives the image output from the first neural network 410, the target neural network 430 is trained to output information indicating that the image (features of the image) is in a high-risk group. Furthermore, the target neural network 430 may use an image pre-processed using a separate object detection technique (e.g., a seed-based region expansion technique). That is, the target neural network 430 predicts the development of lung cancer for the corresponding sample based on a normal image without lung nodules.

Meanwhile, the target neural network 430 may use clinical information of the training data, such as the development time, together with the image output from the first neural network 410 to output information on a time when a disease may develop based on the current time together with information indicating that the image is in a high-risk group.

The second neural network 420 is a neural network that detects an ROI in images of healthy people. The second neural network 420 corresponds to the first neural network 310 described with reference to FIG. 3. The second neural network 420 detects a lung region in the F-18 FDG PET/CT of the lung cancer low risk group (normal group). The second neural network 420 needs to be pre-trained for lung region detection.

When the target neural network 430 receives the image output from the second neural network 420, the target neural network 430 is trained to output information indicating that the image (features of the image) is in a low-risk group. Furthermore, the target neural network 430 may use an image pre-processed using a separate object detection technique (e.g., a seed-based region expansion technique).

Detailed description of a process of training a deep learning network will be omitted. In the target neural network 430, a weight of a neural network layer is optimized through a training process. Of course, while the target neural network 430 is used as an application for determining a probability of developing lung cancer, the result value may be fed back and updated continuously. In the deep learning network, a parameter performs training to reduce a loss function. The loss function may optimize weights of the neural network through the training process. For example, a gradient descent method may be used for the weight optimization.

Figure 5:
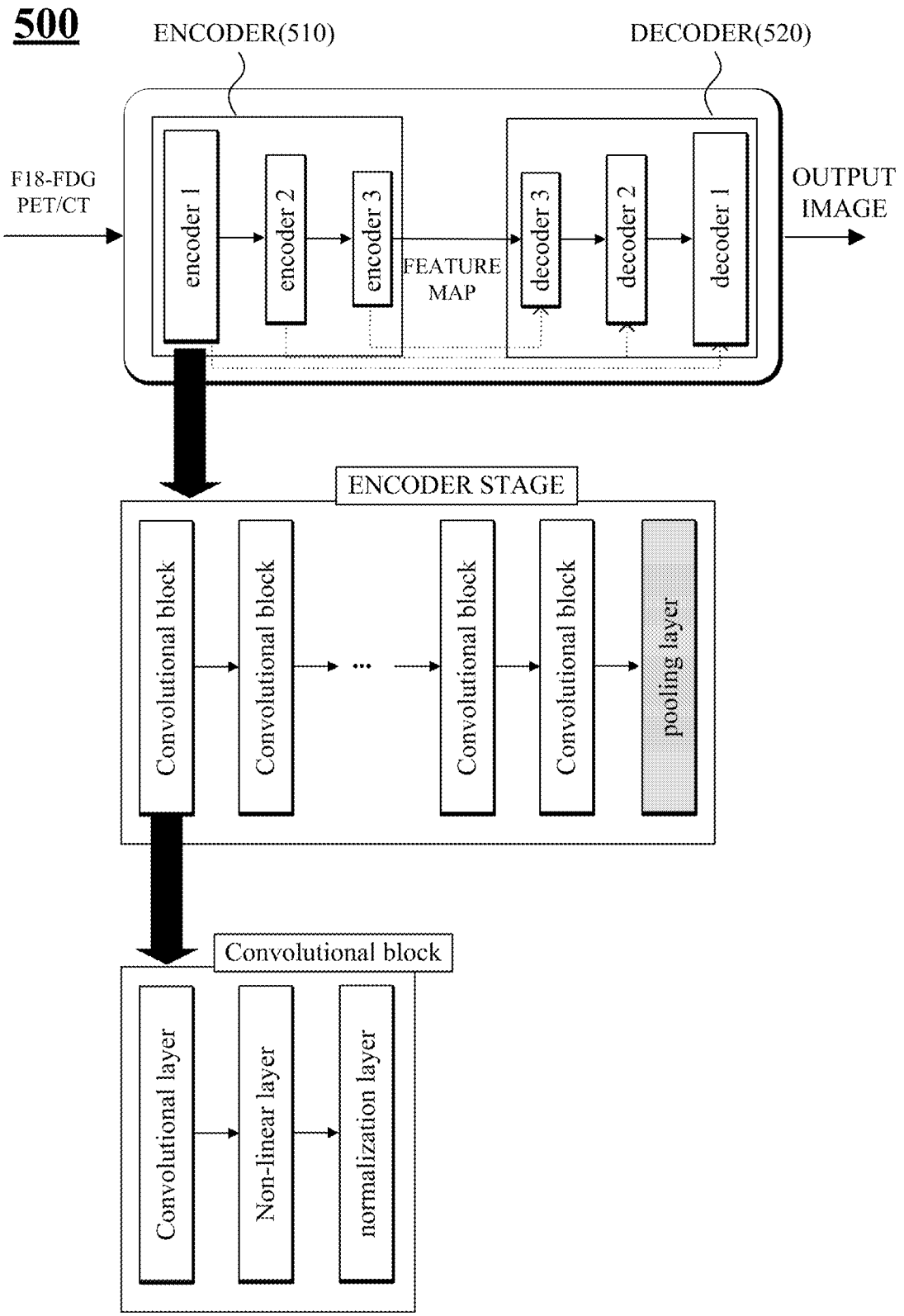
FIG. 5 is an example of a neural network model that generates an image having lung cancer development information.

FIG. 5 is an example of a neural network model 500 that generates an image having lung cancer development information. The neural network model 500 generates an image including information on a probability of developing lung cancer. The neural network model 500 corresponds to a model that extracts feature information from an input image and generates a constant image based on the extracted feature information. Representative examples of such a neural network include an autoencoder, a convolutional encoder-decoder, and the like. FIG. 5 is an example of a convolutional encoder-decoder structure.

The neural network model 500 includes an encoder 510 and a decoder 520.

The encoder 510 receives a medical image (F-18 FDG PET/CT image) and outputs feature information or a feature map. The decoder 520 outputs a specific image based on the received feature information or feature map. An image output from the decoder 520 is called an output image.

The encoder 510 generates a feature map of the medical image and extracts only some effective feature values while reducing a size of the feature map. The decoder 520 increases the size of the feature map based on the effective feature values output from the encoder 510. The decoder 520 finally outputs an output image having the same size as the medical image.

The encoder 510 includes a plurality of encoder stages. FIG. 5 illustrates an example of three encoder stages (encoder 1, encoder 2, and encoder 3).

The encoder stages may include a plurality of convolutional blocks and one pooling layer. One convolutional block includes a convolutional layer, a non-linearity layer, and a normalization layer. A Relu layer may be used as the non-linearity layer. A batch normalization layer may be used as the normalization layer. The operation of each layer is as described above.

The pooling layer may perform max pooling. The pooling layer stores a pixel position having a maximum value and transmits the pixel position to an upsampling layer of the corresponding decoder stage (indicated by a dotted arrow in FIG. 5).

The encoder 510 extracts feature information to be used in determining a probability of developing lung cancer from a medical image. Meanwhile, in order to display a specific region in a medical image, the encoder may use a model capable of recognizing a location of feature information.

The decoder 520 includes a plurality of decoder stages. FIG. 5 illustrates an example of three decoder stages (decoder 1, decoder 2, and decoder 3). As described above, the decoder 520 has a symmetrical structure (mirror image) to the encoder 510. Accordingly, the decoder stage may include one upsampling layer and a plurality of inverse convolutional blocks (equal to the number of convolutional blocks). The operation of the decoder stage is the reverse of the operation of the encoder stage.

The upsampling layer outputs a value of an input feature map to a pixel position of a maximum value received from the maximum pooling layer of the corresponding encoder stage, and outputs a value of "0" outside of the pixel position of the maximum value. The decoder stage has the same number of filters and filter sizes as the convolutional blocks and convolutional layers of the corresponding encoder stage.

The decoder 520 may output an image similar to the input medical image. The output image includes a value reflecting feature information. The output image may express a probability of developing lung cancer (high risk or low risk) in a specific color on the F-18 FDG PET/CT image. Alternatively, the output image may express information on the probability of developing lung cancer in the form of display text on the output image. The information indicated by the output image may vary according to the configuration of the decoder 520 or parameter settings.

Figure 6:
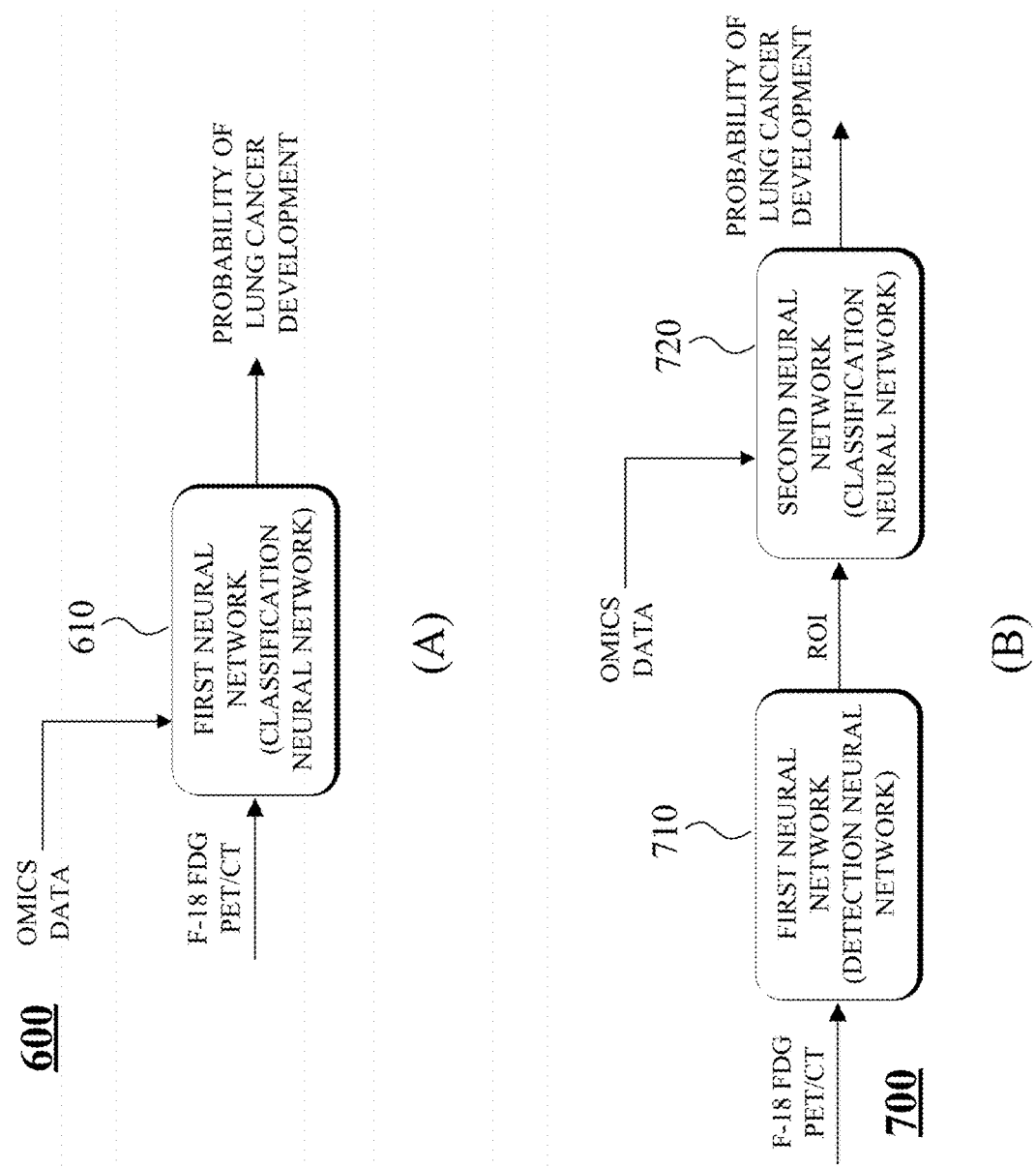
FIG. 6 is an example of a neural network model for predicting development of lung cancer using a medical image and omics data.

FIG. 6 is an example of a neural network model for predicting development of lung cancer using a medical image and omics data.

FIG. 6A is an example of a neural network model 600 for predicting development of lung cancer. FIG. 6A is an example of using one neural network (a first neural network 610). The first neural network 610 receives the F-18 FDG PET/CT image and omics data and outputs the information for determining the probability of developing lung cancer for the corresponding image. The first neural network 610 may output information such as a high risk or a low risk as a probability of developing lung cancer. A neural network for determining a probability of developing lung cancer using a medical image and omics data is also called a classification neural network. The classification neural network may classify a probability of developing lung cancer for a sample (user).

In FIG. 6A, the first neural network 610 may receive only a lung region instead of the entire input image, and process the received lung region. In this case, it may be necessary to perform pre-processing on the input image. For example, the computer device may pre-process the input image using a seed-based region growing technique.

The first neural network 610 may be a model such as a CNN. The first neural network 610 receives a medical image and outputs information on a probability of developing lung cancer, which is a result of analyzing the medical image. The first neural network 610 needs to be pre-trained. The first neural network 610 may be trained using a specific type of training images (either FDG PET or F-18 FDG PET/CT) and information (clinical information) on whether a user from whom the training images were acquired has lung cancer.

As described above, various models may be used for the neural network model. Typically, a CNN may be used. As described above, the training process corresponds to a process of setting parameter values of a CNN layer, in particular, a convolutional layer. The first neural network 610 receives the F-18 FDG PET/CT image and omics data and outputs the information for determining the probability of developing lung cancer for the image. In this case, the first neural network 610 is trained to adjust an output data value for input data based on the clinical information (lung cancer or normal) on the corresponding training data. Accordingly, the medical image and omics data adjust parameter values of the first neural network 610. When a large amount of training data is used, the accuracy of an output result of the first neural network 610 may be higher. For example, by using a tool such as AdamOptimizer, cost function optimization may be performed whenever training data is input. Also, the accuracy may be measured in each training process.

FIG. 6B is another example of a neural network model 700 for predicting development of lung cancer. FIG. 6B is an example of using two neural networks (a first neural network and a second neural network). A first neural network 710 and a second neural network 720 may be different types of deep learning models.

The first neural network 710 detects an ROI in which a desired object exists in a medical image. The first neural network 710 corresponds to a model for detecting (segmenting) a specific region or an object in a medical image. As such, a type of neural network that detects an object in a medical image is called a detection neural network.

The detection neural network identifies an object in a medical image and segments (divides) the object. The detection neural network may be implemented with various types of models. For example, the detection neural network may be a model such as a type of CNN. The detection neural network may have a structure such as an encoder-decoder structure, a FCN, and or like.

The first neural network 710 is for object detection, and detects and divides a specific region based on feature information of a medical image. The first neural network 710 may divide a lung region into an ROI in the F-18 FDG PET/CT image. The first neural network 710 needs to be pre-trained to detect the ROI.

The second neural network 720 outputs information on a probability of developing lung cancer by using the input medical image. The second neural network 720 corresponds to the classification neural network. In this case, the second neural network 720 may use an image output from the first neural network 710 as an input image. That is, the second neural network 720 may output the information on the probability of developing lung cancer based on the lung region.

The second neural network 720 may be a model such as a CNN. The second neural network 720 may receive an ROI detected by the first neural network 710 as an input. Alternatively, the second neural network 720 may receive the entire medical image and analyze the image using the feature information of the ROI. The second neural network 720 outputs information on a probability of developing lung cancer based on the feature information of the ROI and the omics data. The second neural network 720 needs to be pre-trained. The second neural network 720 may be trained using a training image of the ROI and information on a probability of developing lung cancer matching the image.

The second neural network 720 receives the F-18 FDG PET/CT image and omics data and outputs the information for determining the probability of developing lung cancer for the image. In this case, the second neural network 720 is trained to adjust an output data value for input data based on the clinical information (lung cancer or normal) on the corresponding training data. Accordingly, the medical image and omics data adjust parameter values of the second neural network 720. When a large amount of training data is used, the accuracy of an output result of the second neural network 720 may be higher. For example, by using a tool such as AdamOptimizer, cost function optimization may be performed whenever training data is input. Also, the accuracy may be measured in each training process.

Figure 7:
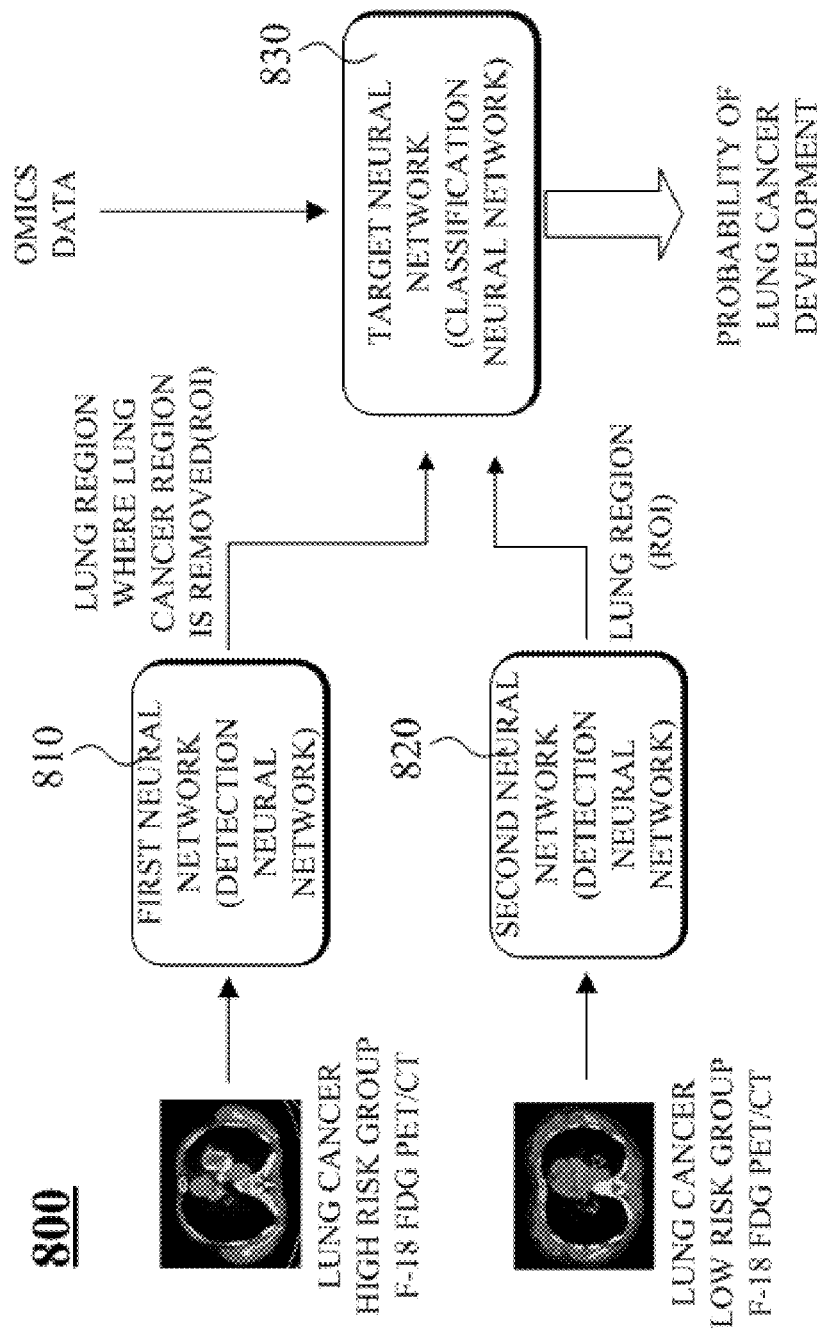
FIG. 7 is another example of the process of training a neural network.

FIG. 7 is another example of a process 800 of training a neural network. FIG. 7 is an example of a process of training a classification neural network. A classification neural network may be trained using medical images and omics data. The medical image may be trained using F-18 FDG PET/CT images of lung cancer patients and F-18 FDG PET/CT images of healthy people.

The training image may be subjected to pre-processing. For example, when the F-18 FDG PET/CT image is used, a PET dicom image and a CT dicom image of 512*512 pixels may be cropped to a size of 256*256 pixels. A determination result of the cropped image may be defined as a two-dimensional one-hot vector. For example, the chest F-18 FDG PET/CT images of healthy people may be classified as a low-risk group and defined as [0,1], and the chest F-18 FDG PET/CT images of lung cancer patients may be classified as a high-risk group and defined as [1,0]. A process of transforming pixel information or text into a single meaningful vector and defining the pixel information is called one-hot encoding.

The first neural network 810 is a neural network for detecting an ROI in images of lung cancer patients. The first neural network 810 detects a lung region in the F-18 FDG PET/CT of the lung cancer high risk group (lung cancer patients). Furthermore, the first neural network 810 detects regions other than lung cancer regions (regions where lung cancer has developed) in the lung region. The first neural network 810 needs to be pre-trained to detect the lung region from which the lung cancer regions have been removed. The first neural network 810 detects regions excluding the lung cancer regions from the images of the lung cancer patients. The regions excluding the lung cancer regions visually correspond to healthy people regions (regions without lung nodules).

A target neural network 830 is the above-described classification neural network. The target neural network 830 outputs information on a probability of developing lung cancer based on the input image and omics data. The target neural network 830 predicts the development of lung cancer for the corresponding sample based on a normal image without lung nodules and omics data.

When the target neural network 830 receives the image output from the first neural network 810 and the omics data for the same sample, the target neural network 430 is trained to output information indicating that the image (features of the image) is in a high-risk group. Furthermore, the target neural network 830 may use an image pre-processed using a separate object detection technique (e.g., a seed-based region expansion technique).

The second neural network 820 is a neural network that detects an ROI in images of healthy people. The second neural network 820 corresponds to the first neural network 310 described with reference to FIG. 3. The second neural network 820 detects a lung region in the F-18 FDG PET/CT of the lung cancer low risk group (normal group). The second neural network 820 needs to be pre-trained for lung region detection.

When the target neural network 830 receives the image output from the second neural network 820 and the omics data, the target neural network 430 is trained to output information indicating that the image (features of the image) is in a low-risk group. Furthermore, the target neural network 830 may use an image pre-processed using a separate object detection technique (e.g., a seed-based region expansion technique).

Detailed description of a process of training a deep learning network will be omitted. In the target neural network 830, a weight of a neural network layer is optimized through a training process. Of course, while the target neural network 830 is used as an application for determining a probability of developing lung cancer, the result value may be fed back and updated continuously. In the deep learning network, a parameter performs training to reduce a loss function. The loss function may optimize weights of the neural network through the training process. For example, a gradient descent method may be used for the weight optimization.

Figure 8:
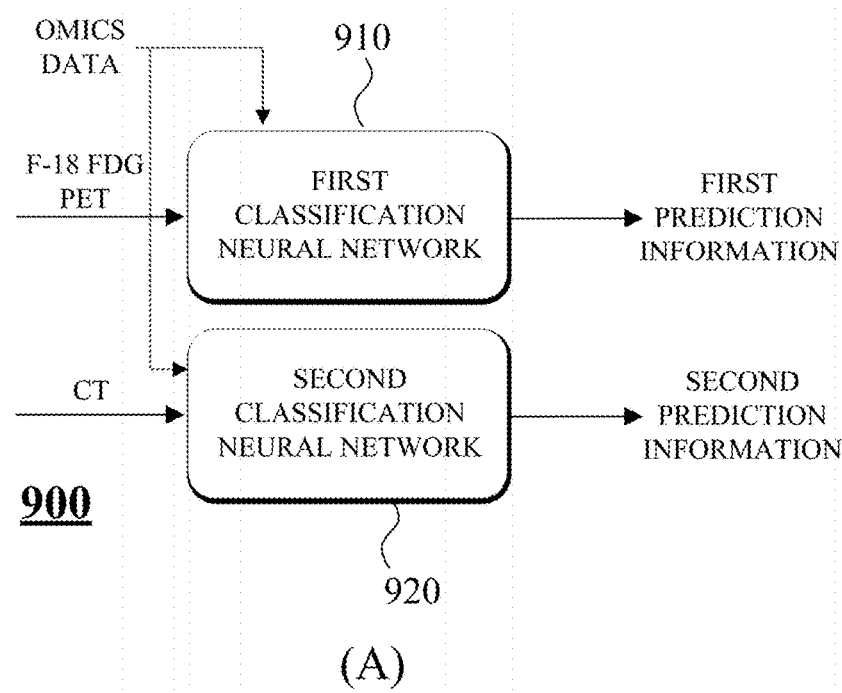
FIG. 8 is still another example of the neural network model for predicting development of lung cancer.
Figure 8:
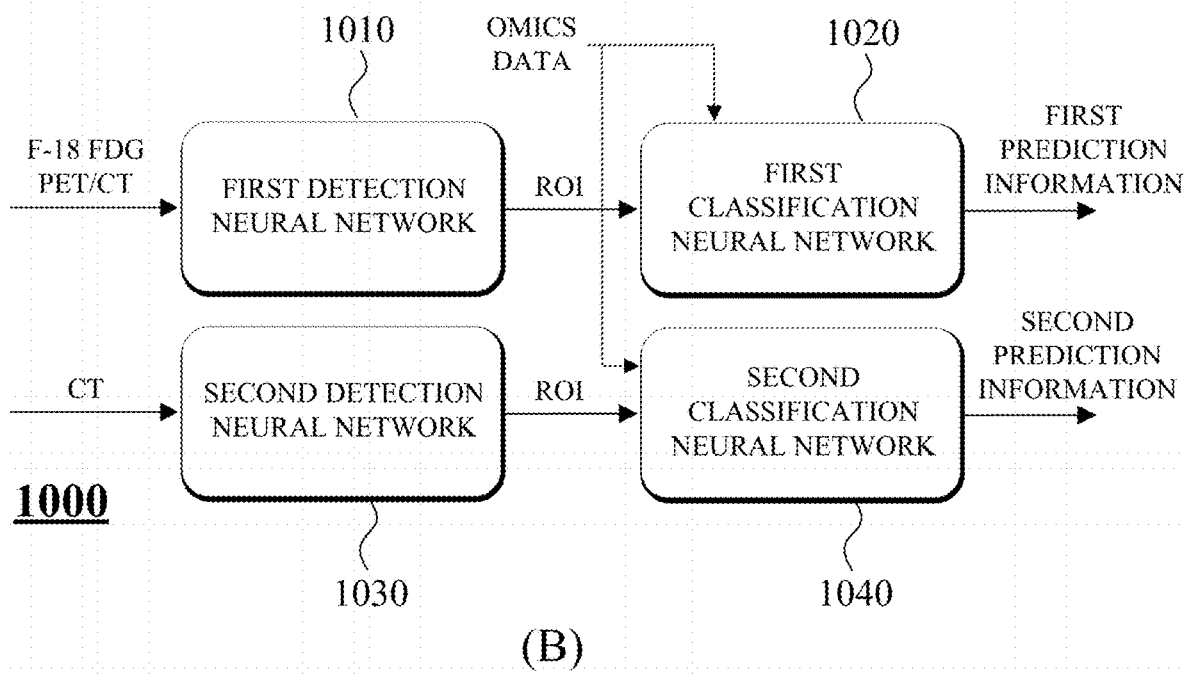

FIG. 8 is still another example of the neural network model for predicting development of lung cancer. The F-18 FDG PET/CT image is an image obtained by registering a PET image and a CT image. Therefore, it is possible to construct a model that separately analyzes the PET image and the CT image, and predicts development of lung cancer based on the analysis result. FIG. 8 illustrates a model for predicting development of lung cancer by using the F-18 FDG PET and CT images separately.

FIG. 8A is an example of a neural network model 900 for predicting development of lung cancer. FIG. 8A is an example of using separate classification neural networks for F-18 FDG PET and CT.

A first classification neural network 910 receives the F-18 FDG PET image and outputs the information for determining the probability of developing lung cancer for the corresponding image. Furthermore, the first classification neural network 910 receives the F-18 FDG PET image and omics data and outputs the information for determining the probability of developing lung cancer for the corresponding image. The first classification neural network 910 may predict development of lung cancer in a corresponding sample based on an input image without lung nodules.

The first classification neural network 910 may output information such as a high risk or a low risk as a probability of developing lung cancer. Furthermore, the first classification neural network 910 may perform multi-classification. For example, the first classification neural network 910 may predict the timing of the probability of developing lung cancer. In this case, the first classification neural network 910 may also provide information on timing, such as a probability of development within 5 years and a probability of development within 3 years for a sample. Of course, for such an output, the training data needs to provide information on a time from imaging to development. Meanwhile, the first classification neural network 910 may output additional information together with information on a probability of developing lung cancer. For example, the first classification neural network 910 may output information such as a 70% or more probability of developing lung cancer within 5 years. The first classification neural network 910 may receive omics data in addition to an image, and may further use the omics data to additionally output information on a probability of development or a survival period. Of course, the first classification neural network 910 needs to be trained using training data having the corresponding information in advance.

The second classification neural network 920 receives the CT image and outputs information for determining a probability of developing lung cancer for the corresponding image. Furthermore, the second classification neural network 920 may receive the CT image and the omics data and output the information for determining the probability of developing lung cancer for the corresponding image. The second classification neural network 920 may predict development of lung cancer in a corresponding sample based on an input image without lung nodules.

The second classification neural network 920 may output information such as a high risk or a low risk as a probability of developing lung cancer. Furthermore, the second classification neural network 920 may perform multi-classification. For example, the second classification neural network 920 may predict the timing of the probability of developing lung cancer. In this case, the second classification neural network 920 may also provide information on timing, such as a probability of development within 5 years and a probability of development within 3 years for a sample. Of course, for such an output, the training data needs to provide information on a time from imaging to development. Meanwhile, the second classification neural network 920 may output additional information together with information on a probability of developing lung cancer. For example, the second classification neural network 920 may output information such as a 70% or more probability of developing lung cancer within 5 years. The second classification neural network 920 may receive omics data in addition to an image, and may further use the omics data to additionally output information on a probability of development or a survival period. Of course, the second classification neural network 920 needs to be trained using training data having the corresponding information in advance.

The analysis device may output diagnostic information on a probability of developing lung cancer based on first prediction information and second prediction information output from the first classification neural network 910 and the second classification neural network 920, respectively. For example, the analysis device may predict a probability of developing lung cancer by comparing a summed value of the first prediction information and the second prediction information with a specific reference value. Alternatively, the analysis device may predict a probability of developing lung cancer based on a summed value (weighted sum) or an averaged value (weighted average) by assigning different weights to the first prediction information and the second prediction information.

In FIG. 8A, the first classification neural network 910 and/or the second classification neural network 920 may receive and process only the lung region instead of the entire input image. In this case, it may be necessary to perform pre-processing on the input image. For example, the computer device may pre-process the input image using a seed-based region growing technique.

The first classification neural network 910 and/or the second classification neural network 920 may be a model such as a CNN. The first classification neural network 910 and the second classification neural network 920 receive a medical image and output information on a probability of developing lung cancer, which is a result of analyzing the medical image. The first classification neural network 910 and the second classification neural network 920 need to be pre-trained. The first classification neural network 910 may be trained using the F-18 FDG PET training images and information (clinical information) on whether a user from whom the training images were acquired has lung cancer. The first classification neural network 910 may receive the F-18 FDG PET/CT image and omics data and output the information for determining the probability of developing lung cancer for the image. In this case, the first classification neural network 910 is trained to adjust an output data value for input data based on the clinical information (lung cancer or normal) on the corresponding training data. Accordingly, the medical image and omics data adjust parameter values of the first classification neural network 910. When a large amount of training data is used, the accuracy of an output result of the first classification neural network 910 may be higher. For example, by using a tool such as AdamOptimizer, cost function optimization may be performed whenever training data is input. Also, the accuracy may be measured in each training process.

The second classification neural network 920 may be trained using the CT training images and the information (clinical information) on whether a user from whom the training images were acquired has lung cancer. The second classification neural network 920 may receive the CT image and omics data and output the information for determining the probability of developing lung cancer for the image. In this case, the second classification neural network 920 is trained to adjust an output data value for input data based on the clinical information (lung cancer or normal) on the corresponding training data. Accordingly, the medical image and omics data adjust parameter values of the second classification neural network 920. When a large amount of training data is used, the accuracy of an output result of the second classification neural network 920 may be higher. For example, by using a tool such as AdamOptimizer, cost function optimization may be performed whenever training data is input. Also, the accuracy may be measured in each training process.

FIG. 8B is another example of a neural network model 1000 for predicting development of lung cancer. FIG. 8B is an example of using two neural networks (a detection neural network and a classification neural network). The detection neural network and the classification neural network may be different types of deep learning models. The detection neural network and the classification neural network are a set of processing input images. FIG. 8B is an example of using separate classification neural networks (a detection neural network and a classification neural network) for F-18 FDG PET and CT.

Detection neural networks 1010 and 1030 detect an ROI in which a desired object exists in a medical image. The detection neural networks 1010 and 1030 correspond to a model for detecting (segmenting) a specific region or an object in a medical image. The detection neural network identifies an object in a medical image and segments (divides) the object. The detection neural network may be implemented with various types of models. For example, the detection neural network may be a model such as a type of CNN. The detection neural network may have a structure such as an encoder-decoder structure, a FCN, or the like.

The first detection neural network 1010 is for object detection, and detects and divides a specific region based on feature information of the F-18 FDG PET image. The first detection neural network 1010 may divide a lung region into the ROI in the F-18 FDG PET/CT image. The first detection neural network 1010 also needs to be pre-trained to detect the ROI.

The first classification neural network 1020 outputs information on a probability of developing lung cancer by using the input medical image. In this case, the first classification neural network 1020 may use an image output from the first detection neural network 1010 as an input image. That is, the first classification neural network 1020 may output the information on the probability of developing lung cancer based on the lung region. The first classification neural network 1020 may predict development of lung cancer in a corresponding sample based on an input image without lung nodules.

The first classification neural network 1020 may be a model such as a CNN. The first classification neural network 1020 may receive an ROI detected by the first detection neural network 1010. Alternatively, the first classification neural network 1020 may receive the entire medical image and analyze the image using the feature information of the ROI. The first classification neural network 1020 outputs information on a probability of developing lung cancer based on the feature information of the ROI and the omics data. The first classification neural network 1020 needs to be pre-trained. The first classification neural network 1020 may be trained using a training image of the ROI and information on a probability of developing lung cancer matching the image.

The first classification neural network 1020 receives the F-18 FDG PET image and outputs the information for determining the probability of developing lung cancer for the corresponding image. Furthermore, the first classification neural network 1020 may receive the F-18 FDG PET image and omics data and output the information for determining the probability of developing lung cancer for the corresponding image.

The first classification neural network 1020 may output information such as a high risk or a low risk as a probability of developing lung cancer. Furthermore, the first classification neural network 1020 may perform multi-classification. For example, the first classification neural network 1020 may predict the timing of the probability of developing lung cancer. In this case, the first classification neural network 1020 may also provide information on timing, such as a probability of development within 5 years and a probability of development within 3 years for a sample. Of course, for such an output, the training data needs to provide information on a time from imaging to development. Meanwhile, the first classification neural network 1020 may output additional information together with information on a probability of developing lung cancer. For example, the first classification neural network 1020 may output information such as a 70% or more probability of developing lung cancer within 5 years. The first classification neural network 1020 may receive omics data in addition to an image, and may further use the omics data to additionally output information on a probability of development or a survival period. Of course, the first classification neural network 1020 needs to be trained using training data having the corresponding information in advance.

The second detection neural network 1030 is for object detection, and detects and divides a specific region based on feature information of the CT image. The second detection neural network 1030 may divide a lung region into the ROI in the CT image. The second detection neural network 1030 also needs to be pre-trained to detect the ROI.

The second classification neural network 1040 outputs information on a probability of developing lung cancer by using the input medical image. In this case, the second classification neural network 1040 may use an image output from the second detection neural network 1030 as an input image. That is, the second classification neural network 1040 may output the information on the probability of developing lung cancer based on the lung region. The second classification neural network 1040 may predict development of lung cancer in a corresponding sample based on an input image without lung nodules.

The second classification neural network 1040 may be a model such as a CNN. The second classification neural network 1040 may receive an ROI detected by the second detection neural network 1030. Alternatively, the second classification neural network 1040 may receive the entire medical image and analyze the image using the feature information of the ROI. The second classification neural network 1040 outputs information on a probability of developing lung cancer based on the feature information of the ROI and the omics data. The second classification neural network 1040 needs to be pre-trained. The second classification neural network 1040 may be trained using a training image of the ROI and information on a probability of developing lung cancer matching the image.

The second classification neural network 1040 receives the CT image and outputs information for determining a probability of developing lung cancer for the corresponding image. Furthermore, the second classification neural network 1040 may receive the CT image and the omics data and output the information for determining the probability of developing lung cancer for the corresponding image.

The second classification neural network 1040 may output information such as a high risk or a low risk as a probability of developing lung cancer. Furthermore, the second classification neural network 1040 may perform multi-classification. For example, the second classification neural network 1040 may predict the timing of the probability of developing lung cancer. In this case, the second classification neural network 1040 may also provide information on timing, such as a probability of development within 5 years and a probability of development within 3 years for a sample. Of course, for such an output, the training data needs to provide information on a time from imaging to development. Meanwhile, the second classification neural network 1040 may output additional information together with information on a probability of developing lung cancer. For example, the second classification neural network 1040 may output information such as a 70% or more probability of developing lung cancer within 5 years. The second classification neural network 1040 may receive omics data in addition to an image, and may further use the omics data to additionally output information on a probability of development or a survival period. Of course, the second classification neural network 920 needs to be trained using training data having the corresponding information in advance.

The analysis device may output diagnostic information on a probability of developing lung cancer based on first prediction information and second prediction information output from the first classification neural network 1020 and the second classification neural network 1040, respectively. For example, the analysis device may predict a probability of developing lung cancer by comparing a sum of the first prediction information and the second prediction information with a specific reference value. Alternatively, the analysis device may predict a probability of developing lung cancer based on a summed value (weighted sum) or an averaged value (weighted average) by assigning different weights to the first prediction information and the second prediction information.

Figure 9:
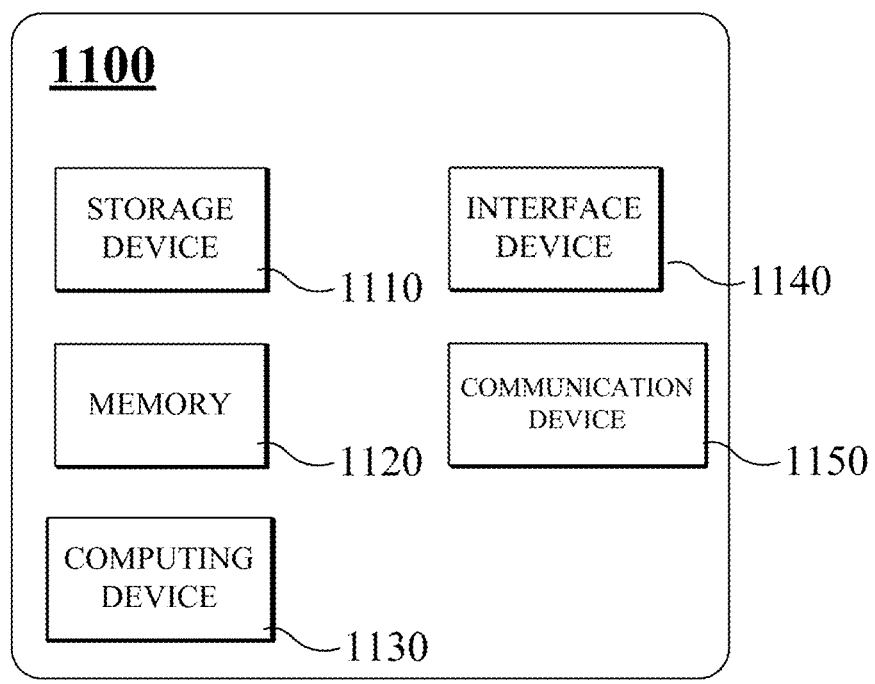
FIG. 9 is an example of a configuration of a device for predicting development of lung cancer using a medical image.

FIG. 9 is an example of a configuration of a device 1100 for predicting development of lung cancer using a medical image. The device 1100 for determining the probability of developing lung cancer corresponds to the above-described analysis device. The device 1100 for determining a probability of developing lung cancer may have a configuration of an analysis server 150 or an analysis PC 180 of FIG. 1.

The device 1100 for determining a probability of developing lung cancer may extract information on a probability of developing lung cancer from a medical image by using the above-described neural network model. The device 1100 for determining a probability of developing lung cancer may be implemented in various physical forms. For example, the device 1100 for determining a probability of developing lung cancer may have the form of a computer device such as a PC, a server of a network, or a dedicated chipset for image processing. The computer device may include a mobile device such as a smart device.

The device 1100 for determining a probability of developing lung cancer includes a storage device 1110, a memory 1120, a computing device 1130, an interface device 1140, and a communication device 1150.

The storage device 1110 stores a neural network model for image processing or analysis. For example, the storage device 1110 may store the above-described classification neural network and/or detection neural network. Furthermore, the storage device 1110 may store a program, a source code, or the like required for image processing. For example, the storage device 1110 may store a program for detecting an ROI in an input image. The storage device 1110 may store the input medical image and the generated output image.

The storage device 1110 may store a detection neural network for detecting a lung region in the medical image. The storage device 1110 may store a classification neural network that classifies the probability of developing lung cancer based on the medical image. Also, the storage device 1110 may store a classification neural network that classifies development of lung cancer based on the medical image and omics data. Furthermore, the storage device 1110 may store a classification neural network that classifies the development of lung cancer based on the medical image and a separate classification neural network that classifies the development of lung cancer based on the omics data.

The storage device 1110 may store a separate detection neural network for each of the F-18 FDG PET and CT images. The storage device 1110 may store a separate classification neural network that classifies the probability of developing lung cancer based on each of the F-18 FDG PET and CT images. Also, the storage device 1110 may store a classification neural network for classifying lung cancer onset by further using the omics data in addition to the medical image.

Also, the storage device 1110 may store a neural network structure further including a neural network such as a decoder that generates a predetermined image based on the feature information of the classification neural network as illustrated FIG. 5.

The memory 1120 may store the medical image received by the device 1100 for determining a probability of developing lung cancer and the data and information generated in the process of generating an output image.

The interface device 1140 is a device that receives predetermined commands and data from the outside. The interface device 1140 may receive the medical image and/or omics data from a physically connected input device or an external storage device. The interface device 1140 may receive various neural network models for image analysis. The interface device 1140 may receive training data, information, and parameter values for generating a neural network model.

The communication device 1150 is a component for receiving and transmitting predetermined information through a wired or wireless network. The communication device 1150 may receive the medical image and/or omics data from an external object. The communication device 1150 may also receive various neural network models and data for model training. The communication device 1150 may transmit the information on the determined probability of developing lung cancer or the output image to an external object.

The communication device 1150 or the interface device 1140 is a device that receives predetermined data or commands from the outside. The communication device 1150 or the interface device 1140 may be referred to as an input device.

The computing device 1130 generates the information on the probability of developing lung cancer or the output image from the medical image by using the neural network model or program stored in the storage device 1110. The computing device 1130 may perform predetermined preprocessing (cropping, ROI detection, etc.) on the medical image. The computing device 1130 may detect the ROI in the medical image using the detection neural network. The computing device 1130 may train the neural network model used in the image processing process by using the given training data.

The computing device 1130 may generate the information on the probability of developing lung cancer from the medical image by using the neural network model built through the above-described process. The computing device 1130 may receive a medical image and output information on a probability of developing lung cancer for a sample. The computing device 1130 may receive the medical image and omics data and output the information on the probability of developing lung cancer for the sample.

Furthermore, the computing device 1130 may determine the probability of developing lung cancer based on the first prediction information output by inputting the medical image to the first classification neural network and the second prediction information output by inputting the omics data to the second classification neural network. In this case, the second classification neural network needs to be pre-trained as a model that receives the omics data and outputs whether or not lung cancer has developed corresponding to clinical information of the sample of the omics data. In the case of using two separate classification neural networks, the case may generally correspond to a model of a forest structure. That is, the computing device 1130 may determine the information on the probability of developing lung cancer based on a value obtained by summing or processing a value output from the first classification neural network and a value output from the second classification neural network. Alternatively, the computing device 1130 may assign different weights to the value output from the first classification neural network and the value output from the second classification neural network to determine the information on the probability of developing lung cancer based on the summed values (weighted sum). In this case, the weights assigned to the output values of each neural network may be determined during the process of training a model.

Furthermore, the computing device 1130 may determine the probability of developing lung cancer based on the first prediction information output by inputting the F-18 FDG PET image to the first classification neural network and the second prediction information output by inputting the CT image to the second classification neural network. As described above, the computing device 1130 may determine the information on the probability of developing lung cancer based on the first prediction information and the second prediction information.

In addition, the computing device 1130 may determine the probability of developing lung cancer based on the first prediction information output by inputting the F-18 FDG PET image and omics data to the first classification neural network and the second prediction information output by inputting the CT image and omics data to the second classification neural network. As described above, the computing device 1130 may determine the information on the probability of developing lung cancer based on the first prediction information and the second prediction information.

Also, before inputting the image to the classification neural network, the computing device 1130 may utilize the detection neural network that detects an analysis target in the input image. That is, the computing device 1130 may first input the input image to the detection neural network to determine the ROI, and input the ROI to the classification neural network to determine the information on the probability of developing lung cancer. As described above, for the detection neural network, a separate neural network may be prepared in advance according to the PET and CT.

The computing device 1130 may be a device such as a processor, an application processor (AP), or a chip having a program embedded therein that processes data and processes a predetermined calculation.

The invention claimed is:

1. A method for determining a probability of developing lung cancer by using an artificial intelligence model, the method comprising:
receiving, by an analysis device, a chest F-18 fluorodeoxyglucose (FDG) positron emission tomography/computed tomography (PET/CT) image for a sample;
inputting, by the analysis device, the chest F-18 FDG PET/CT image to a first classification neural network and outputting prediction information related to development of the lung cancer for the sample; and
predicting, by the analysis device, a probability of developing lung cancer for the sample based on the prediction information,
wherein the first classification neural network is trained using a chest F-18 FDG PET/CT image for a healthy person and a training image excluding a lung cancer region from a chest F-18 FDG PET/CT image for a lung cancer patient.

2. The method of claim 1, wherein the first classification neural network is a convolution neural network (CNN) and outputs the prediction information for classifying the sample into a low-risk group or a high-risk group.

3. The method of claim 1, further comprising generating an image including information on the probability of developing lung cancer by inputting, by the analysis device, feature information output from the first classification neural network to a decoder neural network.

4. The method of claim 1, further comprising inputting, by the analysis device, the chest F-18 FDG PET/CT image to a detection neural network to detect a lung region in the F-18 FDG PET/CT image,
wherein the analysis device inputs the detected lung region to the first classification neural network.

5. The method of claim 1, wherein the training image is generated by inputting the chest F-18 FDG PET/CT image for the lung cancer patient to a separate neural network and extracting a region excluding the lung cancer region from the chest F-18 FDG PET/CT image for the lung cancer patient.

6. The method of claim 1, further comprising:
receiving, by the analysis device, omics data for the sample; and
inputting, by the analysis device, the omics data to a second classification neural network and outputting second prediction information on the probability of developing lung cancer for the sample,
wherein the analysis device predicts the probability of developing lung cancer for the sample based on the prediction information output to the first classification neural network and the second prediction information output from the second classification neural network.

7. The method of claim 1, further comprising receiving, by the analysis device, omics data for the sample,
wherein the analysis device further inputs the omics data to the first classification neural network and outputs the prediction information, and
the first classification neural network changes a coefficient or a weight of a filter for at least one of a plurality of layers based on the omics data for the sample.

8. An analysis device comprising:
an input device configured to receive a chest F-18 fluorodeoxyglucose (FDG) positron emission tomography/computed tomography (PET/CT) image for a sample;
a storage device configured to store a first classification neural network that generates prediction information on a probability of developing lung cancer using the chest F-18 FDG PET/CT image; and
a computing device configured to input the received chest F-18 FDG PET/CT image to the first classification neural network to predict a probability of a subject developing lung cancer,
wherein the first classification neural network is trained using a chest F-18 FDG PET/CT image for a healthy person and a training image excluding a lung cancer region from a chest F-18 FDG PET/CT image for a lung cancer patient.

9. The analysis device of claim 8, wherein the first classification neural network is trained using a PET/CT image labeled with F-18 FDG.

10. The analysis device of claim 8, wherein the first classification neural network is a convolution neural network (CNN) and outputs the prediction information for classifying the sample into a low-risk group or a high-risk group.

11. The analysis device of claim 8, wherein the storage device further stores a detection neural network for detecting a lung region in the chest F-18 FDG PET/CT image, and
the computing device inputs the chest F-18 FDG PET/CT image to the detection neural network to detect a lung region in the chest F-18 FDG PET/CT image and inputs the detected lung region to the first classification neural network.

12. The analysis device of claim 8, wherein the storage device further stores a decoder neural network that receives feature information output from the first classification neural network and generates an image including information on the probability of developing lung cancer, and
the computing device inputs classification information and the feature information output from the first classification neural network to the decoder neural network to generate an image including the classification information.

13. The analysis device of claim 8, wherein the training image is generated by inputting the chest F-18 FDG PET/CT image for the lung cancer patient to a separate neural network and extracting a region excluding the lung cancer region from the chest F-18 FDG PET/CT image for the lung cancer patient.

14. The analysis device of claim 8, wherein the input device further receives omics data for the sample,
   the storage device further stores a second classification neural network that receives the omics data and outputs second prediction information on the probability of developing lung cancer for the sample, and
   the computing device predicts the probability of developing lung cancer for the sample based on the prediction information output to the first classification neural network and the second prediction information output from the second classification neural network.

15. The analysis device of claim 8, wherein the input device further receives omics data for the sample,
   the computing device further inputs the omics data to the first classification neural network and outputs the prediction information, and
   the first classification neural network changes a coefficient or a weight of a filter for at least one of a plurality of layers based on the omics data for the sample.

16. A method for determining a probability of developing lung cancer by using an artificial intelligence model, the method comprising:
   inputting, by an analysis device, a chest F-18 fluorodeoxyglucose (FDG) positron emission tomography (PET) image for a sample to a first classification neural network and outputting first prediction information related to the development of lung cancer for the sample;
   inputting, by the analysis device, a chest computed tomography (CT) image for the sample to a second classification neural network and outputting second prediction information related to the development of lung cancer for the sample; and
   predicting, by the analysis device, a probability of developing lung cancer for the sample based on the first prediction information and the second prediction information,
   wherein the first classification neural network is trained using a chest F-18 FDG PET image for a healthy person and a first training image excluding a lung cancer region from a chest F-18 FDG PET image for a lung cancer patient, and
   the second classification neural network is trained using a chest CT image for a healthy person and a second training image excluding the lung cancer region from a chest CT image for the lung cancer patient.

17. The method of claim 16, further comprising inputting, by the analysis device, the chest F-18 FDG PET image to a first detection neural network to detect a lung region in the chest F-18 FDG PET image, the analysis device inputting the detected lung region to the first classification neural network, and
   inputting, by the analysis device, the chest CT image to a second detection neural network to detect the lung region in the chest CT image, the analysis device inputting the detected lung region in the chest CT image to the second classification neural network.

18. The method of claim 16, wherein the first training image is generated by inputting the chest F-18 FDG PET image for the lung cancer patient to a separate neural network and extracting a region excluding the lung cancer region from the chest F-18 FDG PET image for the lung cancer patient, and
   the second training image is generated by inputting the chest CT image for the lung cancer patient to a separate neural network and extracting a region excluding the lung cancer region from the chest CT image for the lung cancer patient.

19. The method of claim 16, further comprising receiving, by the analysis device, omics data for the sample,
   wherein the analysis device further inputs the omics data to the first classification neural network to output the first prediction information and further inputs the omics data to the second classification neural network to output the second prediction information.

* * * * *